US012023112B2

(12) United States Patent
Prior et al.

(10) Patent No.: US 12,023,112 B2
(45) Date of Patent: Jul. 2, 2024

(54) SYSTEM AND METHOD FOR CONTROLLING A SURGICAL ROBOTIC SYSTEM

(71) Applicant: Covidien LP, Mansfield, MA (US)

(72) Inventors: Scott J. Prior, Shelton, CT (US); Nikolai D. Begg, Wellesley, MA (US); Arvind Rajagopalan Mohan, Dracut, MA (US); Zachary Traina, Verona, NJ (US); Kevin R. Slisz, Old Saybrook, CT (US)

(73) Assignee: Covidien LP, Mansfield, MA (US)

( * ) Notice: Subject to any disclaimer, the term of this patent is extended or adjusted under 35 U.S.C. 154(b) by 537 days.

(21) Appl. No.: 17/196,154

(22) Filed: Mar. 9, 2021

(65) Prior Publication Data

US 2021/0282871 A1 Sep. 16, 2021

Related U.S. Application Data

(60) Provisional application No. 62/987,812, filed on Mar. 10, 2020.

(51) Int. Cl.
| | | |
|---|---|---|
| *A61B 34/30* | (2016.01) | |
| *A61B 17/42* | (2006.01) | |
| *A61B 34/00* | (2016.01) | |
| *A61B 34/37* | (2016.01) | |
| *A61B 90/00* | (2016.01) | |
| *A61B 90/50* | (2016.01) | |

(52) U.S. Cl.
CPC .......... *A61B 34/25* (2016.02); *A61B 17/4241* (2013.01); *A61B 34/37* (2016.02); *A61B 34/74* (2016.02); *A61B 90/361* (2016.02); *A61B 90/37* (2016.02); *A61B 90/50* (2016.02); *A61B 2017/4216* (2013.01); *A61B 2034/252* (2016.02); *A61B 2034/302* (2016.02)

(58) Field of Classification Search
CPC ................ A61B 17/42; A61B 17/4241; A61B 2017/1225; A61B 2017/4216; A61B 34/25; A61B 34/37; A61B 34/74; A61B 34/00; A61B 34/30; A61B 2017/4225
See application file for complete search history.

(56) References Cited

U.S. PATENT DOCUMENTS

| | | |
|---|---|---|
| 6,235,037 B1 | 5/2001 | East et al. |
| 7,090,683 B2 | 8/2006 | Brock et al. |
| 7,214,230 B2 | 5/2007 | Brock et al. |
| 7,713,190 B2 | 5/2010 | Brock et al. |

(Continued)

*Primary Examiner* — Vi X Nguyen
(74) *Attorney, Agent, or Firm* — Carter, DeLuca & Farrell LLP

(57) ABSTRACT

A surgical robotic system includes an image capturing device, a surgical console, a multi-directional indicator, a surgical instrument, and a control tower. The image capturing device is configured to capture an image of a surgical site. The surgical console includes a display configured to display the image of the surgical site. The multi-directional indicator is overlaid over the image of the surgical site on the display. The user input device is operably coupled to the surgical console and configured to generate a user input. The surgical instrument is coupled to a surgical robotic arm. The control tower is configured to receive user input from the user input device and control at least one of the surgical robotic arm or the surgical instrument.

19 Claims, 6 Drawing Sheets

(56) References Cited

U.S. PATENT DOCUMENTS

| | | |
|---|---|---|
| 7,775,972 B2 | 8/2010 | Brock et al. |
| 7,905,828 B2 | 3/2011 | Brock et al. |
| 7,931,586 B2 | 4/2011 | Brock et al. |
| 8,190,238 B2 | 5/2012 | Moll et al. |
| 8,414,598 B2 | 4/2013 | Brock et al. |
| 8,690,893 B2 | 4/2014 | Deitch et al. |
| 8,734,337 B2 | 5/2014 | Deitch et al. |
| 8,808,175 B2 | 8/2014 | Deitch et al. |
| 8,814,789 B2 | 8/2014 | Deitch et al. |
| 9,161,801 B2 | 10/2015 | Hoey |
| 9,358,073 B2 | 6/2016 | Piligian et al. |
| 9,522,252 B2 | 12/2016 | Ahluwalia et al. |
| 9,554,827 B2 | 1/2017 | Omori |
| 10,052,130 B2 | 8/2018 | Richey |
| 10,166,044 B1 | 1/2019 | Richey |
| 10,188,469 B2 | 1/2019 | Iida et al. |
| 2002/0087048 A1 | 7/2002 | Brock et al. |
| 2007/0043338 A1 | 2/2007 | Moll et al. |
| 2007/0197896 A1 | 8/2007 | Moll et al. |
| 2008/0221590 A1 | 9/2008 | Ikeda et al. |
| 2009/0209973 A1 | 8/2009 | East |
| 2012/0016185 A1 | 1/2012 | Sherts et al. |
| 2013/0035537 A1 | 2/2013 | Wallace et al. |
| 2013/0274558 A1 | 10/2013 | Deitch et al. |
| 2013/0317301 A1 | 11/2013 | Deitch et al. |
| 2014/0012305 A1* | 1/2014 | Horton .................... A61L 29/06 606/193 |
| 2014/0025084 A1 | 1/2014 | Taylor et al. |
| 2015/0051608 A1 | 2/2015 | Gaynor |
| 2015/0099924 A1 | 4/2015 | Carey |
| 2015/0133958 A1 | 5/2015 | Singh et al. |
| 2016/0106465 A1 | 4/2016 | Richey |
| 2016/0338783 A1 | 11/2016 | Romo et al. |
| 2017/0112583 A1 | 4/2017 | Cohen et al. |
| 2017/0119483 A1 | 5/2017 | Cohen et al. |
| 2017/0156817 A1 | 6/2017 | Singh et al. |
| 2017/0340353 A1 | 11/2017 | Ahluwalia et al. |
| 2018/0028269 A1 | 2/2018 | Morel et al. |
| 2018/0235719 A1 | 8/2018 | Jarc |
| 2018/0325552 A1 | 11/2018 | Weihe et al. |
| 2018/0325554 A1 | 11/2018 | Prior et al. |
| 2019/0029723 A1 | 1/2019 | Sonoda et al. |
| 2019/0059868 A1 | 2/2019 | Cohen et al. |
| 2019/0059940 A1 | 2/2019 | Cohen et al. |
| 2019/0083187 A1 | 3/2019 | Danitz et al. |
| 2019/0084152 A1 | 3/2019 | Deacon |
| 2019/0201034 A1* | 7/2019 | Shelton, IV ....... A61B 17/1155 |

* cited by examiner

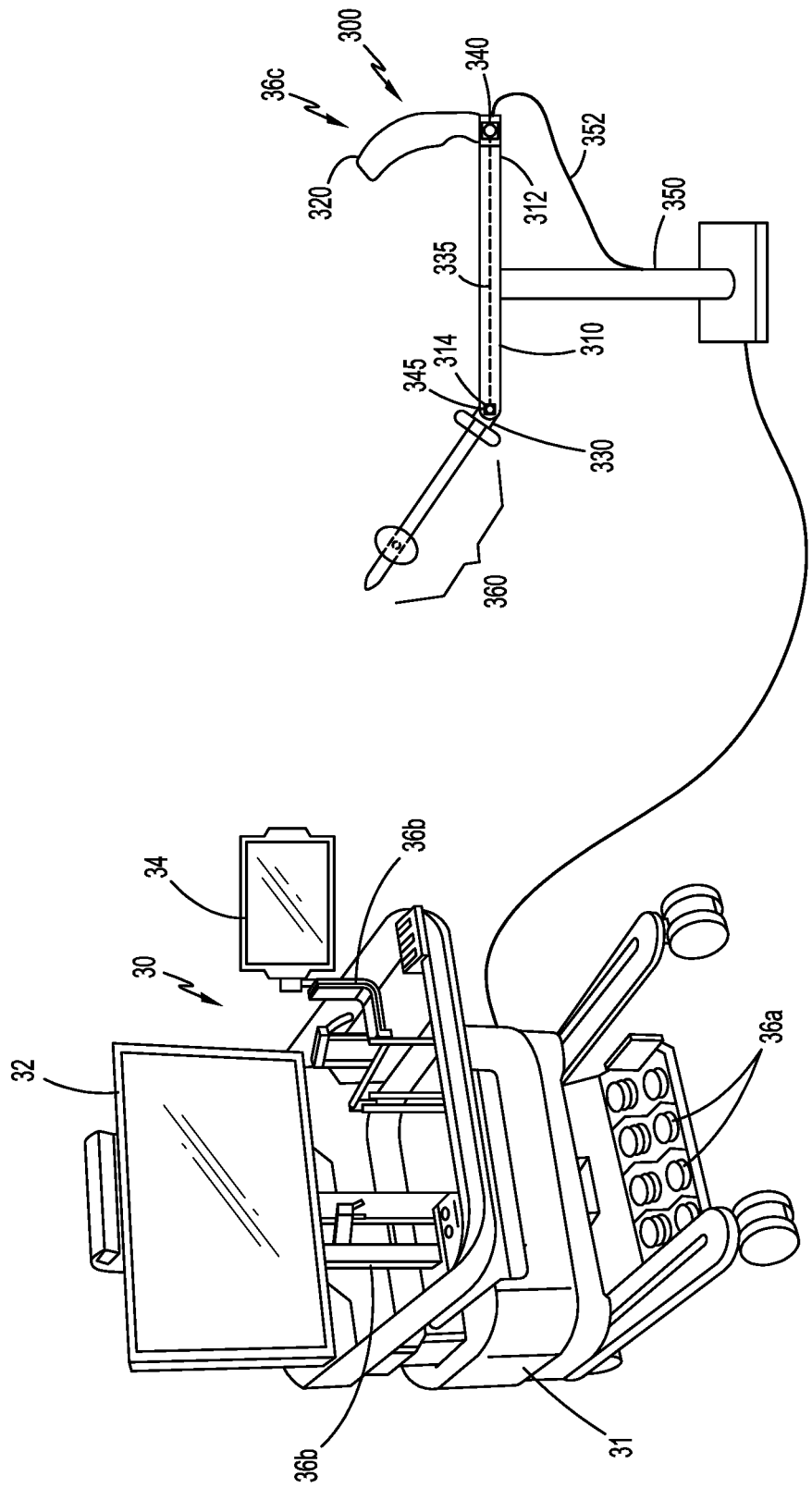

SYSTEM AND METHOD FOR CONTROLLING A SURGICAL ROBOTIC SYSTEM

CROSS REFERENCE TO RELATED APPLICATIONS

This application claims the benefit of U.S. Provisional Application Ser. No. 62/987,812, filed Mar. 10, 2020, the entire contents of which are incorporated by reference herein.

FIELD

The present disclosure is generally related to a robotic surgical system and, more particularly, to systems and methods for controlling a surgical robotic arm and a surgical instrument.

BACKGROUND

Surgical robotic systems are currently being used in medical procedures. Some surgical robotic systems include a surgical console controlling a surgical robotic arm and a surgical instrument coupled to and actuated by the robotic arm.

SUMMARY

This disclosure generally relates to a surgical robotic system including user interface devices for controlling a surgical robotic arm and a surgical instrument.

In one aspect, the present disclosure provides a surgical robotic system including an image capturing device, a surgical console, a multi-directional indicator, a surgical instrument, and a control tower. The image capturing device is configured to capture an image of a surgical site. The surgical console includes a display configured to display the image of the surgical site. The multi-directional indicator is overlaid over the image of the surgical site on the display. The user input device is operably coupled to the surgical console and configured to receive a user input. The surgical instrument is coupled to a surgical robotic arm. The control tower is configured to receive user input from the user input device and control at least one of the surgical robotic arm or the surgical instrument and a position of the surgical instrument is identified on the multi-directional indicator.

In aspects, the control tower may be configured to transcervically manipulate the surgical instrument within a uterus based on the received user input.

In aspects, at least a portion of the surgical instrument within the uterus may not be visible on the image of the surgical site.

In aspects, the multi-directional indicator may include a center position indicator and at least one outer position indicator positioned radially-spaced from the center position indicator.

In aspects, the position of the surgical instrument may correspond to at least one outer position indicator of the at least one outer position indicators that is on the display.

In aspects, the user input device may be a key pad having a plurality of buttons, each button corresponding one of the indicators of the multi-directional indicator.

In aspects, the user input device is a key pad having a plurality of buttons, each button may be assigned a predetermined position of the surgical instrument.

In aspects, the user input device may be a simulated surgical instrument and the user input may be the movement of the simulated surgical instrument.

In aspects, the surgical instrument and the simulated surgical instrument may be uterine manipulators.

In another aspect, the disclosure provides a method of controlling a surgical instrument of a robotic surgical system. The method includes capturing, by an image capturing device, an image of the surgical site; displaying, on a display, the image of the surgical site; displaying, on the display, a multi-directional indicator overlaid over the image of the surgical site; receiving, from a user input device, a user input; transmitting the user input to a control tower of the robotic surgical system; controlling a surgical instrument of the robotic surgical system based on the user input; and identifying a position of the surgical instrument on the multi-directional indicator.

In aspects, controlling the surgical instrument may include transcervically manipulating the surgical instrument within a uterus.

In aspects, at least a portion of the surgical instrument may not be visible on the displayed image of the surgical site.

In aspects, the method may further include highlighting a position of the surgical instrument on the multi-directional indicator.

In aspects, the multi-directional indicator may include a center position indicator and at least one outer position indicator positioned radially-spaced from the center position indicator.

In aspects, the user input device may be a key pad having buttons corresponding to the multi-directional indicator and receiving the user input may include receiving an actuation signal from one of the buttons.

In aspects, the buttons of the key pad may be assigned predetermined positions of the surgical instrument and controlling the surgical instrument may include moving the surgical instrument to the predetermined position corresponding to the button from which the actuation signal is received.

In aspects, the user input device may be a simulated surgical instrument and receiving the user input may include receiving an input based upon movement of the simulated surgical instrument.

In aspects, the surgical instrument and the simulated surgical instrument may be uterine manipulators.

In another aspect, the disclosure provides a surgical robotic system including an image capturing device, a surgical console, a uterine manipulator, and a simulated uterine manipulator. The image capturing device is configured to capture an image of the surgical site. The surgical console includes a display configured to display the image of the surgical site. The uterine manipulator is coupled to a surgical robotic arm and configured to enable manipulation of a uterus. The simulated uterine manipulator is operably coupled to the surgical console and configured to transmit movement of the simulated uterine manipulator to a control tower such that the control tower causes movement of the uterine manipulator based on the received movement of the simulated uterine manipulator.

In aspects, the display may be further configured to overlay a multi-directional indicator over the image of the surgical site. The multi-directional indicator includes a center position indicator and at least one outer position indicator positioned radially-spaced from the center position indicator. The position of the uterine manipulator may be visually indicated on the multi-directional indicator by highlighting a corresponding one of the at least one outer position indicators of the multi-directional indicator.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 4A is a perspective view of an exemplary surgical console configured for use with the surgical robotic system of FIG. 1, with a surgical instrument as a user interface device;

DETAILED DESCRIPTION

Figure 1:
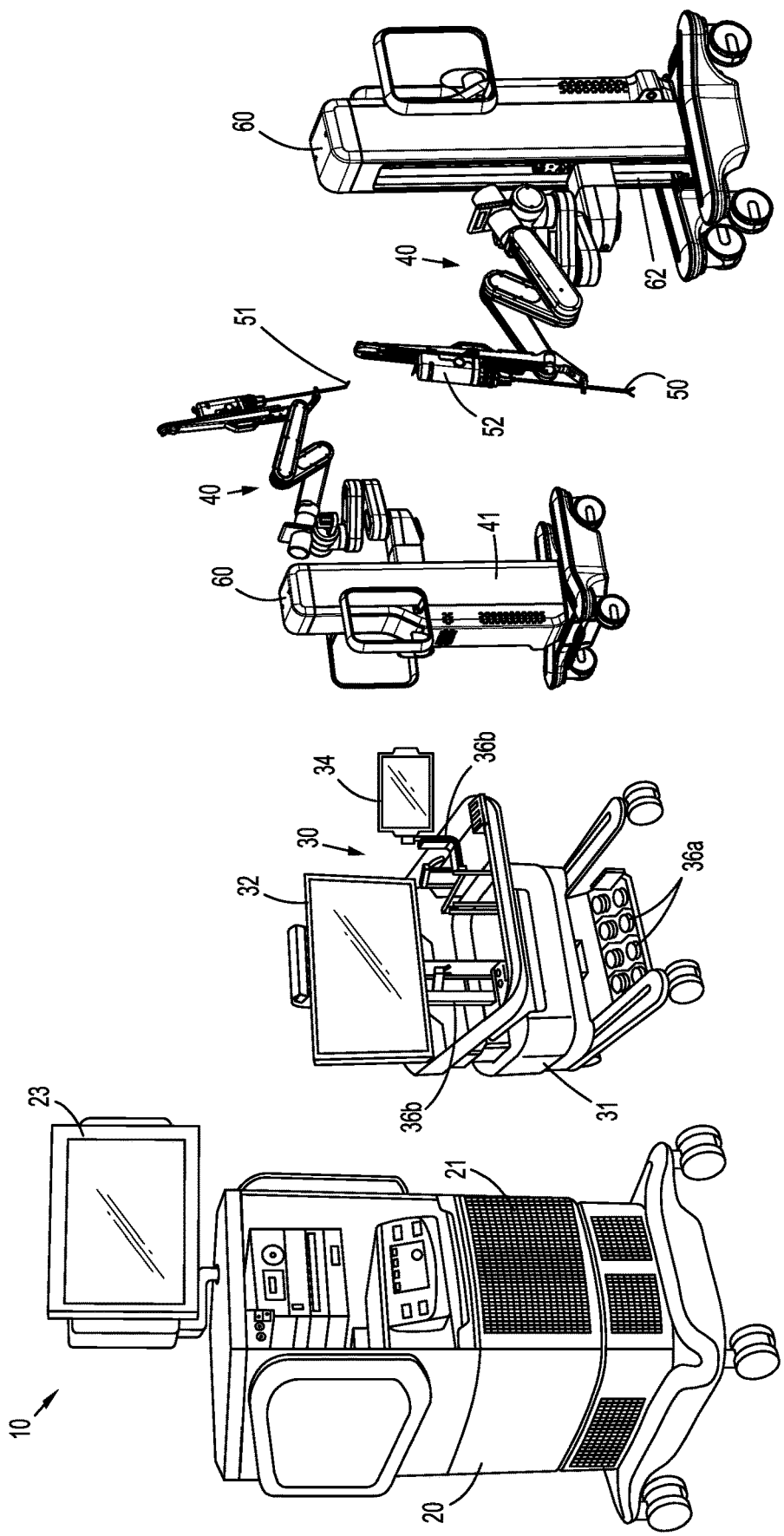
FIG. 1 is a schematic illustration of a surgical robotic system including a control tower, a surgical console, and at least one surgical robotic arm in accordance with the present disclosure.

The presently disclosed surgical robotic systems and methods are described in detail with reference to the drawings, in which like reference numerals designate identical or corresponding elements in each of the several views.

As used herein, the term "clinician" refers to a doctor, nurse, surgeon, or other care provider and may include support personnel.

The term "distal," as used herein, refers to that portion of the surgical instrument or component thereof, farther from the clinician, while the term "proximal" refers to that portion of the surgical instrument, or component thereof, closer to the clinician.

As used herein, the term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 802.15.4-2003 standard for wireless personal area networks (WPANs)).

The present disclosure is directed to systems and methods for controlling a surgical robotic arm and a surgical instrument. More specifically, the present disclosure provides user interface devices of a robotic surgical system configured to manipulate a surgical instrument coupled to a robotic arm of the robotic surgical system.

Various surgical instruments utilized to perform transcervical diagnostic and/or therapeutic surgical tasks may benefit from being capable of attachment to a surgical robotic arm. Uterine manipulators, for example, are often utilized in laparoscopic hysterectomy procedures for, among other tasks, positioning the uterus such that a colpotomy can be performed and the uterus removed. Uterine manipulators are typically controlled manually at the bedside or between the patient's legs. Thus, when adapted for control by a clinician at a surgical console, the controls of the uterine manipulators must be adapted for use in robotic surgical systems.

Referring initially to FIG. 1, a surgical robotic system 10 includes a control tower 20, which is connected to all of the components of the surgical robotic system 10 including a surgical console 30 and one or more robotic arms 40 having actuators, links, and/or joints. Each of the robotic arms 40 includes a surgical instrument 50, 51 removably coupled thereto. Each of the robotic arms 40 is also coupled to a movable cart 60. In some instances, the robotic arm 40 may be coupled to the surgical table (not shown).

Figure 3:
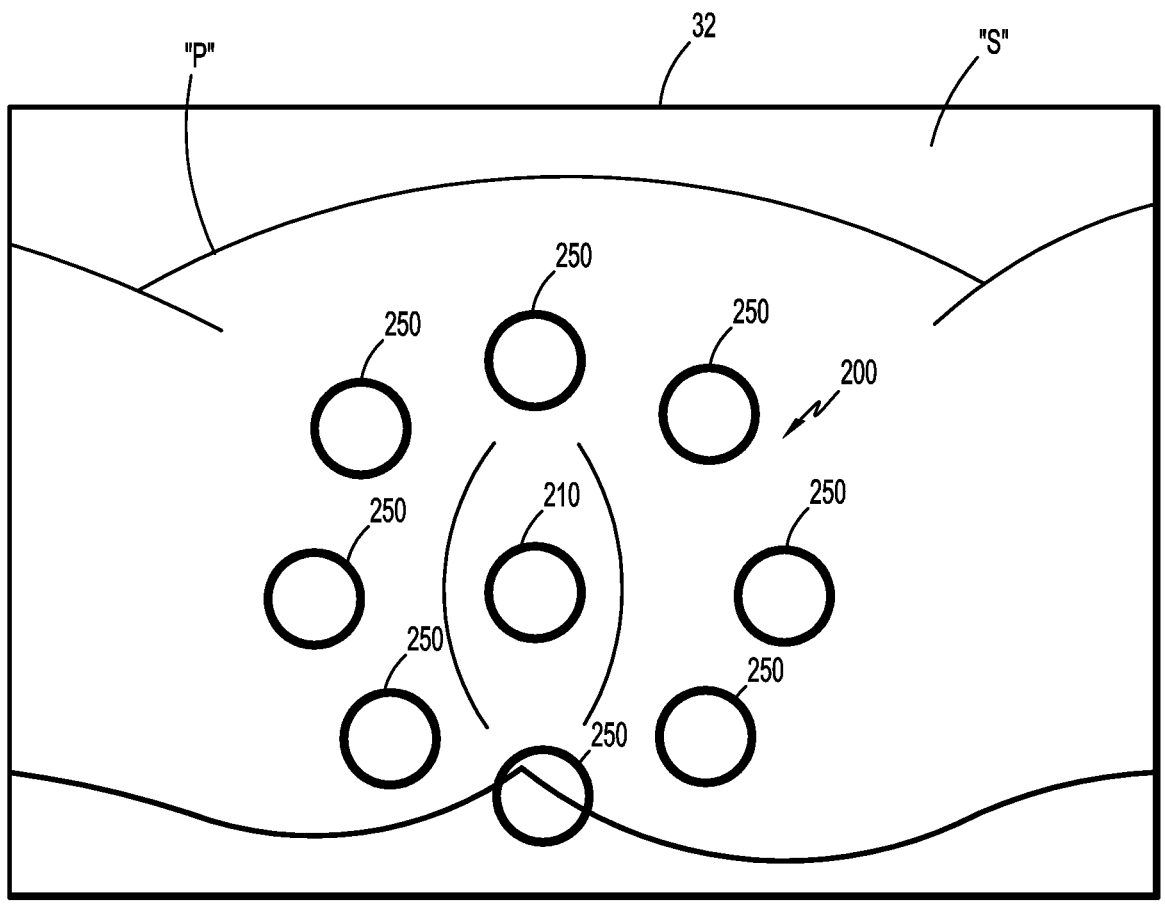
FIG. 3 is a front view of a display showing a surgical site with a multi-directional configuration overlaid over the surgical site.

The surgical instrument 50 is configured for use during minimally invasive or open surgical procedures. The surgical instrument 51 may be a camera configured to capture video of the surgical site "S" (FIG. 3). The camera 51 may be a stereoscopic camera and may be disposed along with the surgical instrument 50 on the robotic arm 40 or, as shown, may be disposed on a separate robotic arm 40.

The surgical console 30 includes a first display 32, which displays a video feed of the surgical site "S" provided by camera 51, and a second display device 34, which displays a user interface for controlling the surgical robotic system 10. Alternatively, the user interface and video feed may be displayed on the same display, e.g., using a split-screen, side-bar(s), overlay, etc. The surgical console 30 includes a plurality of user input devices e.g., user interface devices, such as foot pedals 36a and a pair of handle controllers 36b which are used by a clinician to remotely control or teleoperate the surgical instrument 100 and/or the robotic arms 40.

The control tower 20 includes a display 23, which may be a touchscreen, and outputs on the graphical user interfaces (GUIs). The control tower 20 also acts as an interface between the surgical console 30 and one or more robotic arms 40. In particular, the control tower 20 is configured to control the robotic arms 40, such as to move the robotic arms 40 and the corresponding surgical instruments 50, 51, based on a set of programmable instructions and/or input commands from the surgical console 30, in such a way that robotic arms 40 and the surgical instruments 50, 51 execute a desired movement sequence in response to input from the user interface devices, e.g., foot pedals 36a and the handle controllers 36b.

Each of the control tower 20, the surgical console 30, and the robotic arm 40 includes a respective computer 21, 31, 41. The computers 21, 31, 41 are interconnected to each other using any suitable communication network based on wired or wireless communication protocols. The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Each of the computers 21, 31, 41 of the surgical robotic system 10 may include a plurality of controllers, which may be embodied in hardware and/or software. The computer 21 of the control tower 20 includes a controller (not shown) configured to receive data from the computer 31 of the surgical console 30 about the current position, orientation, and/or state of the interface devices e.g., the handle controllers 36b and the foot pedals 36a. The computer 21 processes these input positions to determine desired drive commands for each of the robotic arm 40 and/or the instrument drive unit 52 and communicates these to the computer 41 of the robotic arm 40. The computer 21 may also receive actual joint angles and uses the received actual joint angles to determine force feedback commands that are transmitted back to the computer 31 of the surgical console 30 to provide haptic feedback through the interface devices.

The computer 41 includes a plurality of controllers, namely, a main cart controller (not shown), a setup arm controller (not shown), a robotic arm controller (not shown), and an instrument drive unit (IDU) controller (not shown). The main cart controller receives and processes joint commands from the computer 21 and communicates them to the controllers of computer 41, namely the setup arm controller, the robotic arm controller, and the IDU controller. The main cart controller also manages instrument exchanges and the overall state of the movable cart 60, the robotic arm 40, and the instrument drive unit 52. The main cart controller also communicates actual joint angles back to the computer 21.

The setup arm controller controls the setup arm 62 and calculates desired motor movement commands (e.g., motor torque) for the pitch axis and controls the brakes. The robotic arm controller controls the robotic arm 40 and calculates desired motor torques required for gravity compensation, friction compensation, and closed loop position control of the robotic arm 40. The robotic arm controller calculates a movement command based on the calculated torque. The calculated motor commands are then communicated to one or more of the actuators in the robotic arm 40. The actual joint positions are then transmitted by the actuators back to the robotic arm controller.

The IDU controller receives desired joint angles for the surgical instrument 50, such as wrist and jaw angles, and computes desired currents for the motors in the instrument drive unit 52. The IDU controller calculates actual angles based on the motor positions and transmits the actual angles back to the main cart controller.

The robotic arm 40 is controlled as follows. Initially, a pose of the user interface device controlling the robotic arm 40, e.g., the handle controller 36b, is transformed into a desired pose of the robotic arm 40 through a hand eye transform function executed by the computer 21. The hand eye function, as well as other functions described herein, is/are embodied in software executable by the computer 21 or any other suitable controller described herein. The pose of one of the user interface devices may be embodied as a coordinate position and role-pitch-yaw ("RPY") orientation relative to a coordinate reference frame, which is fixed to the surgical console 30. The desired pose of the surgical instruments 50, 51 are relative to fixed frames on the robotic arm 40. The pose of the user interface device is then scaled by a scaling function executed by the computer 21. In some instances, the coordinate position may be scaled down and the orientation may be scaled up by the scaling function. In addition, the computer 21 also executes a clutching function, which disengages the user interface device from the robotic arm 40. In particular, the main cart computer 21 stops transmitting movement commands from the user interface device to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the user interface device and is then passed by an inverse kinematics function executed by the computer 21. The inverse kinematics function calculates angles for the joints of the robotic arm 40 that achieve the scaled and adjusted pose input by the user interface device. The calculated angles are then passed to the robotic arm controller, which includes a joint axis controller having a proportional-derivative (PD) controller, the friction estimator module, the gravity compensator module, and a two-sided saturation block, which is configured to limit the commanded torque of the motors of the joints of the robotic arm 40.

Figure 2:
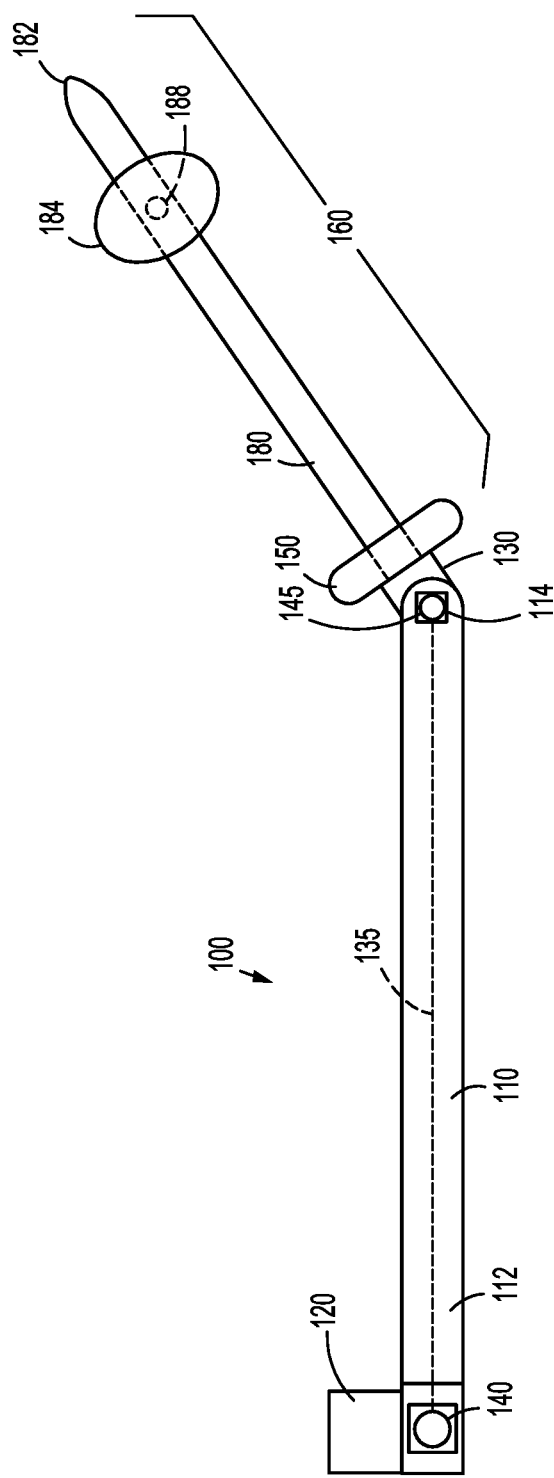
FIG. 2 is a perspective view of an exemplary surgical instrument coupled to the surgical robotic arm of FIG. 1.

With reference to FIG. 2, in some configurations, the surgical instrument 50 may be a uterine manipulator 100 including a body 110, a robotic arm interface housing 120, a distal connector 130 disposed at a distal end portion 114 of the body 110, and an end effector assembly 160 extending distally from the distal connector 130. The uterine manipulator 100 also includes a distal pivot 145 pivotably coupling the distal connector 130 with the body 110 at the distal end portion 114 of the body 110. An actuation linkage 135, e.g., a cable, rod, or other suitable link, extends through the body 110 and operably couples the robotic arm 40 via the robotic arm interface housing 120 with the distal connector 130 to enable pivoting of the distal connector 130 relative to the body 110. The uterine manipulator 100 may be operably coupled to the robotic arm 40 via a proximal pivot 140 disposed at the proximal end portion 112 of the body 110. More specifically, drive commands from the computer 21 to the computer 41 of the robotic arm 40 pivot the body 110 relative to the robotic arm interface housing 120 about proximal pivot 140 to thereby pivot distal connector 130 relative to the body 110 about the distal pivot 145, based on user input from the user interface device.

The end effector 160 of the uterine manipulator 100 includes a stop 150, an elongated shaft 180, a balloon 184, and an aperture 188. The stop 150 is configured to abut a cervix (not shown) to stabilize the uterus (not shown), to define a maximum insertion depth of the uterine manipulator 100, and/or prevent the loss of insufflation gases from the uterus. The elongated shaft 180 defines an atraumatric distal tip 182 and is configured to facilitate insertion of the end effector assembly 160 through the cervix and into the uterus. The balloon 184 is supported on the elongated shaft 180 proximally spaced from the atraumatric distal tip 182 and adapted to connect to a fluid source (not shown) and aperture 188. The aperture 188 is in communication with the interior of the balloon 184 to enable selective inflation or deflation of the balloon 184. The inflation of the balloon 184 causes the balloon 184 to contact the interior wall of the uterus to stabilize the end effector assembly 160, thereby allowing manipulation of the end effector assembly 160 via the user interface devices and pivots 140, 145.

The uterine manipulator 100, as noted above, includes robotic arm interface housing 120 disposed at a proximal end portion 112 of the body 110. As also noted above, the uterine manipulator 100 includes proximal pivot 140 pivotably coupling the robotic arm interface housing 120 with the body 110 at the proximal end portion 112 of the body 110. The actuation linkage 135 may extend through the body 110 and operably couples robotic arm interface housing 120 with the distal connector 130 to enable pivoting of the distal connector 130 relative to the body 110. More specifically, the robotic arm interface housing 120 may be operably coupled to the robotic arm 40 and pivoting of the robotic arm interface housing 120 relative to the body 110 about the proximal pivot 140 correspondingly pivots the distal connector 130 relative to the body 110 about the distal pivot 145 according to drive commands from the computer 21 to the computer 41 of the robotic arm 40 based on user input from the user interface device.

With reference to FIG. 3, in conjunction with FIG. 1, computer 31 may be further configured to display a multi-directional configuration 200 overlaid on the video feed of the surgical site "S," e.g., of the patient "P," from the camera 51 on first display 32 of the surgical console 30. The multi-directional configuration 200 has one or more position indicators, the one or more positions indicators including a center position indicator 210 and one or more outer position indicators 250. Each of the outer position indicators 250 is positioned radially-spaced from the center position indicator 210 and designates a different direction. The radial positioning of each of the outer position indicators 250 may be finely or coarsely adjusted to account for different axes, directions, and/or patient anatomies. This may be accomplished on first display 32 or on a separate screen or GUI. Likewise, instead of overlying the multi-directional configuration 200, such may be provided on a separate screen or GUI.

The computer 31 is further configured to identify the position of the uterine manipulator 100 and highlight on the first display 32 the center position indicator 210 or the relevant outer position indicator(s) 250 of the multi-directional configuration 200 corresponding to the position of the uterine manipulator 100. In this manner, even where the uterine manipulator 100 or portions thereof are not visible on the video feed of the surgical site "S," the position and/or orientation thereof can be readily identified via the multi-directional configuration 200.

With reference to FIG. 4A, the user interface device may include a simulated surgical instrument 36c, e.g., a simulated uterine manipulator 300 coupled to a stand 350 disposed in front of the surgical console 30 and/or directly coupled to the surgical console 30 and configured to be manipulated. The simulated uterine manipulator 300 has a body 310, a manually manipulatable handle 320 disposed at a proximal end portion 312 of the body 310, a distal connector 330 disposed at a distal end portion 314 of the body 310, and an end effector assembly 360 extending distally from the distal connector 330. The uterine manipulator 300 also includes a proximal pivot 340 pivotably coupling the handle 320 with the body 310 at a proximal end portion 312 of the body 310 and a distal pivot 345 pivotably coupling the distal connector 330 with the body 310 at the distal end portion 314 of the body 310. An actuation linkage 335, e.g., a cable, rod, or other suitable link, extends through the body 310 and operably couples the handle 310 with the distal connector 330 to enable pivoting of the distal connector 330 relative to the body 310 in response to pivoting of the handle 320 relative to the body 310, similarly as detailed above with respect to uterine manipulator 100 (FIG. 2). The surgical console 30 is further configured to receive the manipulation of the simulated uterine manipulator 300 in all axes by the clinician via a wired connection, e.g., using electrical cable 352, or via a wireless connection to remotely control or teleoperate the uterine manipulator 100 (FIG. 2) in a corresponding axis. In some configurations, distal portions of the uterine manipulator 300 are omitted, e.g., a distal portion of body 310 and components distal thereof, and replaced with suitable simulation components, mechanically and/or electrically controlled, to provide similar resistance and tactile feedback during manipulation of handle 320 as if the distal components were provided.

Figure 4B:
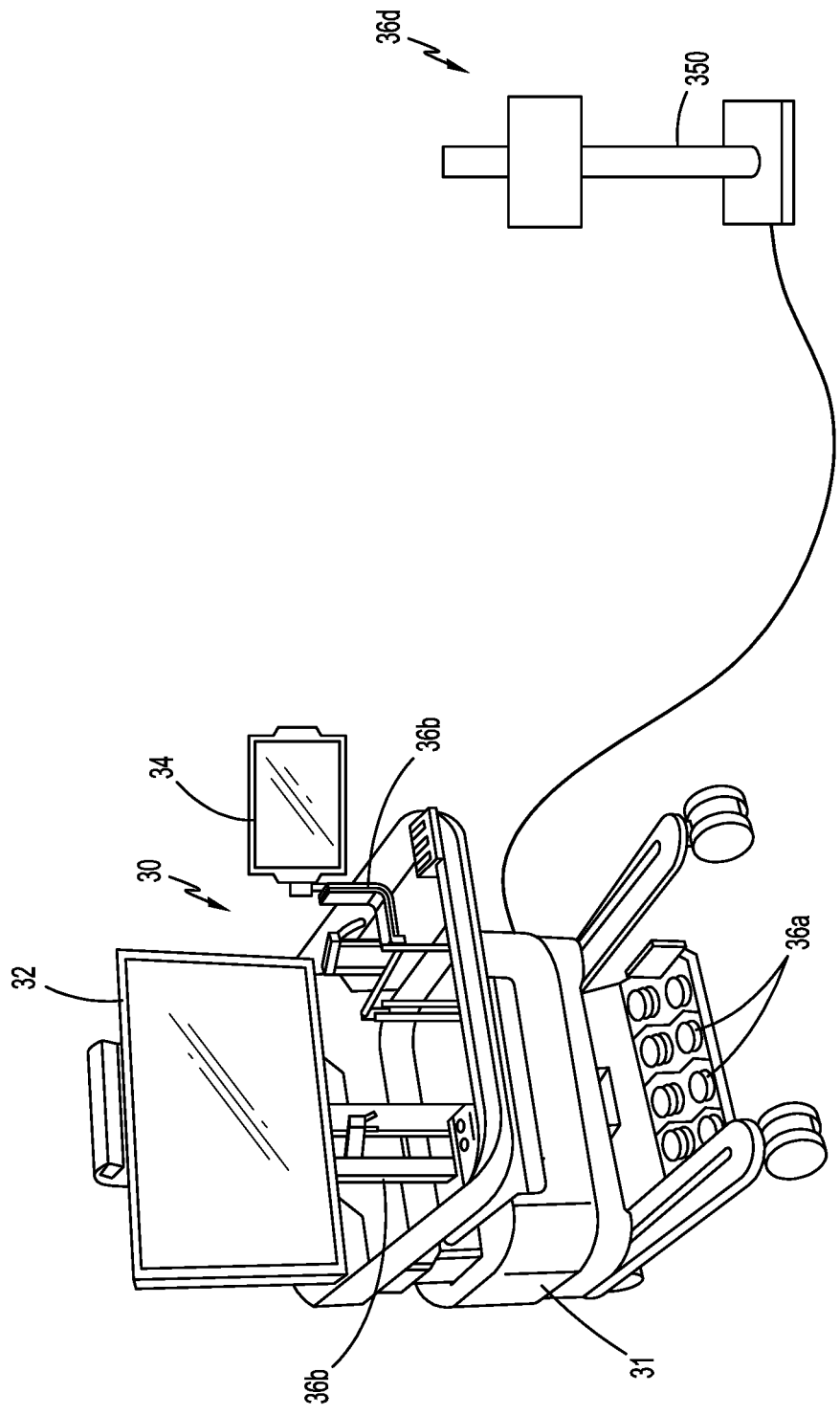
FIG. 4B is a perspective view of another exemplary surgical console configured for use with the surgical robotic system of FIG. 1, with a joystick as the user interface device.

Referring to FIG. 4B, the user interface device may, in other configurations, be a joystick 36d, or any other suitable selection mechanism, coupled to the stand 350 and/or directly to the surgical console 30 and configured to receive manipulation of the joystick 36d by the clinician via wired or wireless connection to remotely control or teleoperate the uterine manipulator 100 (FIG. 1) attached to the robotic arm 40. Alternatively, or additionally, the foot pedals 36a and the handle controllers 36b may be used to remotely control or teleoperate the uterine manipulator 100 (FIG. 1) by manipulating the foot pedals 36a or the handle controller 36b. The controls 36a, 36b may be configured to operate as if the uterus was centered therebetween and directly movable by manipulation of the foot pedals 36a or the handles controller 36b.

Figure 4C:
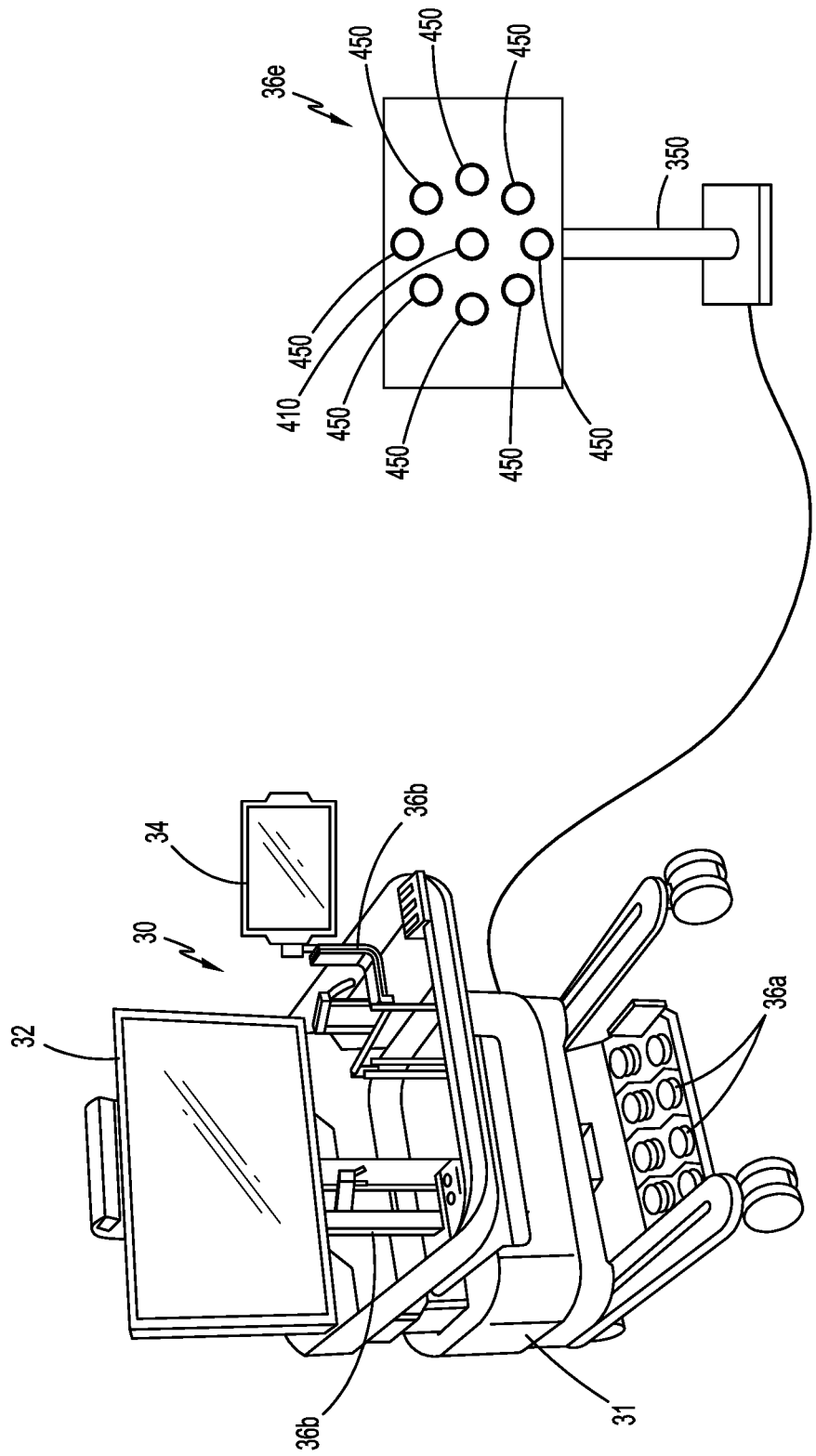
FIG. 4C is a perspective view of another exemplary surgical console configured for use with the surgical robotic system of FIG. 1, with a key pad as the user interface device.

With reference to FIG. 4C, in conjunction with FIG. 3, the user interface device may be a keypad 36e coupled to the stand 350 and/or directly to the surgical console 30 and configured to remotely control or teleoperate the uterine manipulator 100 (FIG. 1) by the clinician via wired or wireless connection. The keypad 36e includes one or more buttons including a center button 410 and at least one outer button 450. The keypad 36e may be configured in a "drum pad" style responsive to touch actuation of the buttons 410, 450. The center button 410 of the keypad 36e corresponds to the center position 210 of the multi-directional configuration 200 and each of the outer buttons 450 corresponds to a corresponding one of the outer positions 250 of the multi-directional configuration 200. The keypad 36e is further configured to be programmed to remotely control or teleoperate the uterine manipulator 100 (FIG. 1) to a direction or position corresponding to the position of the multi-directional configuration 200 such that touch actuation of a button 410, 450 effects movement or manipulation of the uterine manipulator 100 (FIG. 1) in a corresponding direction indicated by the multi-directional configuration 200. The buttons 410, 450 of the keypad 36e may be universally or selectively pre-programmed for all surgical procedures or for each individual surgical procedure or clinician. The buttons 410, 450 of the keypad 36e may also be custom programmed prior to, during, and/or after the surgical procedure. This may be accomplished by the clinician selecting one or more desired locations/positions on the second display device 34 displaying the surgical site "S," manually positioning the uterine manipulator 100 (FIG. 1) in one or more desired locations/positions, and assigning the desired locations/positions to the buttons 410, 450 of the keypad 36e. Other suitable methods of preselecting desired locations are also contemplated. The center button 410 of the keypad 36e may be assigned as a home position or initial position of the uterine manipulator or any other desired location/position.

Referring generally to FIGS. 1-4C, in operation, the robotic surgical system 10 is initialized and the uterine manipulator 100 is coupled to the robotic arm 40. The uterine manipulator 100, led by the end effector assembly 160, is inserted through the vagina, cervix, and into the uterus such that the stop 150 of the uterine manipulator 100 abuts or is disposed in proximity to the cervix with the end effector assembly 160 extending therethrough into the uterus. The balloon 184 is inflated to expand into contact with the interior wall of the uterus, thereby positioning the uterine manipulator 100.

An image of the surgical site is captured by camera 51 and displayed on display 32. The multi-directional configuration 200 is displayed over the image of the surgical site provided on display 32, centering the center position indicator 210 of the multi-directional configuration 200 over the vagina (or other chosen central anatomy) in the image of the surgical site.

In order to perform a surgical task, the clinician manipulates the simulated uterine manipulator 300, the joystick 36d, the foot pedals 36a, and/or handles controller 36b in a desired angular direction, to thereby pivot the distal connector 130 of the uterine manipulator 100 relative to the body 110 such that the end effector assembly 160 is articulated in the desired angular direction causing the uterus to be moved in the desired angular direction, due to the stabilization of the end effector assembly 160 within the uterus. In some instances, the clinician actuates a button of the keypad 36e corresponding to a desired position of the uterine manipulator 100, to thereby articulate the end effector assembly 160 of the uterine manipulator 100 to the desired position indicated by the clinician.

Once the uterine manipulator 100 is actuated to the desired angular direction or desired position, the position or angular direction of the end effector 160 of the uterine manipulator 100 is identified and highlighted on the multi-directional configuration 200. In particular, the center position indicator 210 or outer position indicators 250 of the multi-direction configuration 200 is highlighted based on one or more of the actual position, the actual angular direction, or the pre-programmed position assigned by the clinician.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. It should also be understood that, depending on the example, certain acts or events of any of the processes or methods described herein may be performed in a different sequence, may be added, merged, or left out altogether (e.g., all described acts or events may not be necessary to carry out the techniques). Accordingly, the subject matter of the present disclosure is not limited by what has been particularly shown and described.

What is claimed is:

1. A surgical robotic system comprising:
an image capturing device configured to capture an image of a surgical site;
a surgical console including a display configured to display the image of the surgical site;
a multi-directional indicator overlaid over the image of the surgical site on the display;
a user input device operably coupled to the surgical console and configured to receive a user input;
a surgical instrument coupled to a surgical robotic arm; and
a control tower configured to receive user input from the user input device and to manipulate the surgical instrument within the surgical site based on the received user input,
wherein a position of the surgical instrument is identified on the multi-directional indicator, and
wherein at least a portion of the surgical instrument is not visible on the image of the surgical site.

2. The surgical robotic system according to claim 1, wherein the control tower is configured to transcervically manipulate the surgical instrument within a uterus based on the received user input.

3. The surgical robotic system according to claim 2, wherein the at least a portion of the surgical instrument within the uterus is not visible on the image of the surgical site.

4. The surgical robotic system according to claim 1, wherein the multi-directional indicator includes a center position indicator and at least one outer position indicator positioned radially-spaced from the center position indicator.

5. The surgical robotic system according to claim 4, wherein the position of the surgical instrument corresponds to at least one outer position indicator of the at least one outer position indicators that is highlighted on the display.

6. The surgical robotic system according to claim 4, wherein the user input device is a key pad having a plurality of buttons, each button corresponding to one of the indicators of the multi-directional indicator.

7. The surgical robotic system according to claim 1, wherein the user input device is a key pad having a plurality of buttons, each button assigned a predetermined position of the surgical instrument.

8. The surgical robotic system according to claim 1, wherein the user input device is a simulated surgical instrument and the user input is the movement of the simulated surgical instrument.

9. The surgical robotic system according to claim 8, wherein the surgical instrument and the simulated surgical instrument are uterine manipulators.

10. A surgical robotic system comprising:
an image capturing device configured to capture an image of a surgical site;
a surgical console including a display configured to display the image of the surgical site;
a multi-directional indicator overlaid over the image of the surgical site on the display, wherein the multi-directional indicator includes a center position indicator and at least one outer position indicator positioned radially-spaced from the center position indicator;
a user input device operably coupled to the surgical console and configured to receive a user input;
a surgical instrument coupled to a surgical robotic arm; and
a control tower configured to receive user input from the user input device and control at least one of the surgical robotic arm or the surgical instrument,
wherein a position of the surgical instrument is identified on the multi-directional indicator.

11. The surgical robotic system according to claim 10, wherein the control tower is configured to manipulate the surgical instrument based on the received user input.

12. The surgical robotic system according to claim 11, wherein at least a portion of the surgical instrument is not visible on the image of the surgical site.

13. The surgical robotic system according to claim 11, wherein the control tower is configured to transcervically manipulate the surgical instrument within a uterus based on the received user input.

14. The surgical robotic system according to claim 13, wherein at least a portion of the surgical instrument within the uterus is not visible on the image of the surgical site.

15. The surgical robotic system according to claim 10, wherein the position of the surgical instrument corresponds to at least one outer position indicator of the at least one outer position indicators that is highlighted on the display.

16. The surgical robotic system according to claim 15, wherein the user input device is a key pad having a plurality of buttons, each button corresponding to one of the indicators of the multi-directional indicator.

17. The surgical robotic system according to claim 10, wherein the user input device is a key pad having a plurality of buttons, each button assigned a predetermined position of the surgical instrument.

18. The surgical robotic system according to claim 10, wherein the user input device is a simulated surgical instrument and the user input is the movement of the simulated surgical instrument.

19. The surgical robotic system according to claim 18, wherein the surgical instrument and the simulated surgical instrument are uterine manipulators.

* * * * *